US010995612B2

(12) United States Patent
Rouchon et al.

(10) Patent No.: US 10,995,612 B2
(45) Date of Patent: May 4, 2021

(54) METHOD FOR EXPLOITATION AND/OR MONITORING OF AN AQUIFER COMPRISING AT LEAST ONE DISSOLVED GAS

(71) Applicant: IFP Energies nouvelles, Rueil-Malmaison (FR)

(72) Inventors: Virgile Rouchon, Vaucresson (FR); Valerie Beaumont, Montreuil Sous Bois (FR); Bruno Garcia, Neuilly sur Seine (FR); Isabelle Durand, Rueil Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 601 days.

(21) Appl. No.: 15/824,638

(22) Filed: Nov. 28, 2017

(65) Prior Publication Data

US 2018/0080319 A1    Mar. 22, 2018
US 2021/0079790 A9    Mar. 18, 2021

(30) Foreign Application Priority Data

Nov. 28, 2016  (FR) ..................................... 16/61.559

(51) Int. Cl.
*E21B 49/08*  (2006.01)
*G01N 33/00*  (2006.01)
(Continued)

(52) U.S. Cl.
CPC .......... *E21B 49/088* (2013.01); *E21B 49/086* (2013.01); *G01N 33/004* (2013.01); (Continued)

(58) Field of Classification Search
CPC ...... E21B 49/088; E21B 49/086; E21B 49/08; G01N 33/004; G01N 33/005; G01N 33/18; G01N 33/0036; G01N 33/24; G06N 7/00
See application file for complete search history.

(56) References Cited

U.S. PATENT DOCUMENTS

| 2014/0250999 | A1* | 9/2014 | Lawson | E21B 49/02 73/152.23 |
| 2014/0288853 | A1* | 9/2014 | Dreyfus | G01N 1/00 702/27 |
| 2014/0356068 | A1* | 12/2014 | Andritsos | B63C 7/006 405/60 |

OTHER PUBLICATIONS

Xiaoqin Zhang, et al., "Complexity Analysis of Dichotomy Method in Solving the Approximated Solution of Equations," IEEE College of Mathematics & Information science, Wenzhou University, p. 257-259 (Year: 2011).*

(Continued)

*Primary Examiner* — Rehana Perveen
*Assistant Examiner* — Steven W Crabb
(74) *Attorney, Agent, or Firm* — Fitch, Even, Tabin & Flannery LLP

(57) ABSTRACT

The invention is a method for the exploitation and/or monitoring of an underground formation having at least one reservoir comprising water, at least one gas species of interest and at least one atmospheric isotope of at least one rare gas present in dissolved form in the water of the reservoir. The method includes at least (1) taking at least one gas sample at the level of at least one collection of water from the reservoir, the collection being at the surface and the sampling being carried out to avoid any contamination with the air; (2) measuring at least the concentration of at least the gas species and the concentration of at least an atmospheric isotope of the rare gas in the gas sample; (3) determining the concentration of the gas species of interest dissolved in the water of the reservoir by a model.

15 Claims, 2 Drawing Sheets

(51) Int. Cl.
  *G01N 33/18* (2006.01)
  *G01N 33/24* (2006.01)
  *G06N 7/00* (2006.01)

(52) U.S. Cl.
  CPC ....... *G01N 33/005* (2013.01); *G01N 33/0036* (2013.01); *G01N 33/18* (2013.01); *G01N 33/24* (2013.01); *G06N 7/00* (2013.01); *E21B 49/08* (2013.01)

(56) References Cited

OTHER PUBLICATIONS

Lin Y. Hu, "Gradual Deformation and Iterative Calibration of Gausssian-Related Stochastic Models," International Association for Mathematical Geology, pp. 87-108 (Year: 2000).*
Preliminary Search Report (2 pages).

Gilfillan S M V et al: "The noble gas geochemistry of natural CO2 gas reservoirs from the Colorado Plateau and Rocky Mountain provinces, USA", Geochimica Et Cosmochimica Acta, Pergamon Press, New York, NY, US, vol. 72, No. 4, (Feb. 15, 2008).

Arslan Sebnem et al: "Analysis of groundwater dynamics in the complex aquifer system of Kazan Trona, Turkey, using environmental tracers and noble gases", Hydrogeology Journal, Springer Berlin Heidelberg, Berlin/Heidelberg, vol. 23, No. 1, (Sep. 17, 2014).

A. Paonita et al: "Dissolved inert gases (He, Ne and N2) as markers of groundwater flow and degassing areas at Mt Etna volcano (Italy)", Chemical Geology., vol. 443, (Sep. 15, 2016).

Bruno Garcia et al: "The CO2-vadose project: Numerical modeling to perform a geochemical monitoring methodology and baseline performance assessment for various geochemical variables (gas flux, gas composition, stable isotopes and noble gases) in the carbonate vadose zone", International Journal of Greenhouse Gas Control, vol. 14, (Jan. 5, 2013).

* cited by examiner

METHOD FOR EXPLOITATION AND/OR MONITORING OF AN AQUIFER COMPRISING AT LEAST ONE DISSOLVED GAS

CROSS REFERENCE TO RELATED APPLICATIONS

Reference is made to French Application No. 16/61.559 filed Nov. 28, 2016, which is incorporated herein by reference in its entirety.

BACKGROUND OF THE INVENTION

Field of the Invention

The present invention relates to the field of exploration and exploitation of an underground formation comprising a water reservoir in which at least one gas of interest is dissolved, or the monitoring of an underground formation of this kind.

Description of the Prior Art

The following documents will be cited in the rest of the description:
Duan, Z., Moller, N., Greenberg, J., Weare, J H., 1992. The prediction of methane solubility in natural waters to high ionic strength from 0 to 250° C. and from 0 to 1600 bar. Geochimica et Cosmochimica Acta, 56, 1451-1460.
Duan, Z., Mao, S., 2006. A thermodynamic model for calculating methane solubility, density, and gas phase composition of methane-bearing aqueous fluids from 273 to 253 K and from 1 to 2000 bar. Geochimica et Cosmochimica Acta, 70, 3369-3386.
Gevantman, L H., 2003, Solubility of selected gases in water. CRC Handbook of Chemistry and Physics, 8, Pages 86-87.
Gonzalez-Penagos, F., Rouchon, V., Guichet, Moretti, I., Accepted. The distribution of thermogenic, bacterial and inorganic fluid sources in the petroleum systems of the Llanos Basin (Colombia)—Insights from the noble gases and carbon stable isotopes. MARINE AND PETROLEUM GEOLOGY, 71, 391-408.
Johnson R L., Pankow, J F., Cherry, J A., 1987. Design of a Ground-Water Sampler for Collecting Volatile Organics and Dissolved Gases in Small-Diameter Wells. Ground Water, 25-4, 448-454.
Kampbell, D H., Vandegrift, S A., 1998. Analysis of Dissolved Methane, Ethane, and Ethylene in Ground Water by a Standard Gas Chromatographic Technique. Journal of Chromatographic Science, 36, 253-256.
Kontogeorgis, G M., Voutsas, E C., Yakoumis, J V., and Tassios, D P., 1996. An equation of state for associating fluids. Industrial Engineering Chemistry Research, 35, 4310-4318.
Magnier, C., Rouchon, V., Bandeira, C., Goncalves, R., Miller, D., Dino, R., 2011. Surface and Subsurface Geochemical Monitoring of an EOR-CO2 Field: Buracica, Brazil. OIL & GAS SCIENCE AND TECHNOLOGY-REVUE D IFP ENERGIES NOUVELLES, 67 (2), 355-372. Soreide, I. and Whitson, C., 1992. Peng-Robinson predictions for hydrocarbons, CO2, N2 and H2S with pure water and NaCl brine. Fluid Phase Equilibria, 77, 217-240.
Sundaram, B., Feitz, A., Caritat, P. de, Plazinska, A., Brodie, R., Coram, J. and Ransley, T., 2009. Groundwater Sampling and Analysis—A Field Guide. Geoscience Australia, Record 2009/27 95 pp.
Whitson, C H., 1988. Fluid Sampling and analysis of laboratory data. Norsk Hydro PVT Analyses Manual, Chapter 3 Fluid Sampling and Laboratory data.

The methods known to date for quantifying the concentration of a gas species present in dissolved form in a water reservoir of an underground formation most often require a liquid sample to be taken directly from within the water reservoir. For example see the technique that takes a bottom sample, followed by a PVT study (see for example Johnson et al., 1987, Whitson, 1988) or an analysis of the dissolved gases in a sample of water at the surface (see for example Sundaram et al., 2009, Kampbell and Vandegrift, 1998). These techniques have the considerable drawback of requiring a sample to be taken from the bottom or the surface allowing the bottom conditions to be preserved when the sample is brought up to the surface, which may be technically difficult to implement (notably it is necessary to ensure that the sample is not contaminated by the fluids present in the well, by the air at the surface, as well as take steps against fractionation of the composition of the dissolved gases between the liquid and vapor phases during decompression of the fluid) and which may prove expensive, particularly when sampling must be repeated over time (if monitoring a site for geological storage of a gas for example, where a sampling device must be lowered repeatedly in the drilled well).

A technique is also known (see for example Whitson, 1998) that determines the concentration of a gas species present in dissolved form in a water reservoir by combining an analysis of gas samples taken at the surface of the formation of interest and well tests, notably measurements of the flow rates of water and gas at the surface of the well. Although this technique has the great advantage of not requiring sampling directly from within the water reservoir of interest, it nevertheless requires the existence of at least one well, and the execution of well tests, notably measurements of the flow rates of water and gas at the surface of the well. Implementation of this technique that requires well tests may therefore be complex and expensive, especially when the well tests must be repeated over time (if monitoring a site for geological storage of a gas for example, where well tests must be carried out repeatedly over time).

SUMMARY OF THE INVENTION

In general, the present invention relates to the quantification of a gas of interest present in dissolved form in a water reservoir, such as an aquifer, a thermal resurgence, etc.

In general, the gas of interest may be a gas injected into the formation for the purpose of underground storage thereof (it could be for example $CO_2$, or methane), a gas resulting from industrial contamination (a gas from storage of waste for example, called "landfill gas"), or else resulting from natural contamination ("marsh gas" or "stray gas"), or a gas produced naturally (such as methane).

Thus, the information contained in the geochemical composition of the gases dissolved in a water reservoir may provide information about the origin of a gas resource and the content of this resource. The origin and content of a gaseous species dissolved in the water of a reservoir provide essential information for (1) examining the exploitation of the species in question or (2) understanding whether contamination of the reservoir is due to industrial activity (pollution of an aquifer for example) or to a natural process (seismicity, hot springs, etc.). Moreover, the gas burden of water reservoirs may be essential information for the production of a thermal energy reservoir (geothermal energy).

A particular application of the present invention relates to the geological storage of $_{CO2}$ in an underground formation. European directive 2009/31/CE requires permanent storage that is safe for the environment, preventing and controlling any return of $CO_2$ and of associated substances to the surface, while limiting the disturbances of the underground environment. Thus, a rate of escape of $_{CO2}$ of 0.01% per year at a site for geological sequestration of $CO_2$ is the maximum tolerated according to this directive. In order to comply with current regulations, and to contribute to society's acceptance of this technology, it seems necessary to elaborate techniques for monitoring the sites with geological storage of $CO_2$, for detecting and quantifying any escapes.

The present invention determines the concentration of a gas species of interest in a water reservoir in a manner that is simple, noninvasive and inexpensive. In particular, the method according to the invention does not necessarily require drilling (in the case of a natural resurgence, for example), and in any case does not require bottom sampling or well tests.

In fact, the present invention is based on an analysis of gases resulting from the degassing (natural or artificial) of an underground water reservoir and sampled at the surface, to allow quantitative determination of the composition of gas dissolved in the reservoir.

The method according to the invention notably allows easier monitoring of natural or industrial contamination, with various gaseous species, of these waters situated near sites of resource exploration or exploitation, such as activities of gas storage, gas production, geothermal energy activities, or other activities.

THE METHOD ACCORDING TO THE INVENTION

The invention relates to a method for the exploitation and/or monitoring of an underground formation having at least one reservoir comprising water, at least one gas species and at least one atmospheric isotope of at least one rare gas that are present in dissolved form in the water of the reservoir. The method according to the invention comprises at least the following steps:

i—taking at least one gas sample at the level of a collecting zone of the water of the reservoir located at the surface of the formation, the sampling being carried out in such a way as to avoid any contamination with the air;

ii—measuring at least the concentration of at least the gas species and the concentration of at least the atmospheric isotope of the rare gas in the gas sample;

iii—determining the concentration of the gas species present in the reservoir in dissolved form by a model of the concentration of the gas species in dissolved form, the model being a function of the concentration of at least the gas species in the gas sample and of the concentration of the atmospheric isotope in the gas sample.

According to one embodiment of the invention, the atmospheric isotope of the rare gas may be the $^{20}Ne$ isotope of neon, the $^{36}Ar$ isotope of argon or the $^{84}Kr$ isotope of krypton.

According to an embodiment of the invention according to which the collection of the water from the reservoir is carried out at least by a well connecting the surface of the formation and the water reservoir, the sampling may be carried out by an impervious sampling cylinder placed at the head of the well.

Alternatively, when the collection is passive collection, carried out at the level of a natural resurgence of the water of the reservoir at the surface that is not equipped with a well, the sampling may be carried out by an impervious sampling cylinder comprising at least one tubular body connected to a funnel, the gas sample being taken at the level of the funnel.

According to one embodiment of the invention, the model may be based on an analytical method based on a formula of the type:

$$C^j_T = (1/K_{Hj} + C^j_{air}/(C^j_v \cdot K_{Hi}^{amb}) - 1/K_{Hi}^z) \cdot C^j_v$$

where:
$C^j_T$ is the concentration of the gas species of interest j;
$K_{Hj}$ is the Henry constant relating to the gas species of interest j;
$C^j_{air}$ is the concentration of the atmospheric isotope i in the air;
$C^j_v$ is the concentration of the atmospheric isotope i measured in the sample;
$K_{Hi}^{amb}$ is the Henry constant relating to the atmospheric isotope i for ambient surface conditions;
$K_{Hi}^z$ is the Henry coefficient of the atmospheric isotope i at depth z;
$C^j_v$ is the concentration of the gas species of interest j measured in the sample.

According to one embodiment of the invention, the model may be based on an iterative numerical method comprising solving a direct problem at each of the iterations of the iterative numerical method and optimization of an objective function measuring a difference between the measured concentrations and concentrations calculated by the solving of the direct problem.

Advantageously, the direct problem may be solved by at least one equation of state.

According to one embodiment of the invention, the optimization of the objective function may be carried out by a dichotomy method.

Other features and advantages of the method according to the invention will become clear on reading the following description of nonlimiting embodiment examples.

DETAILED DESCRIPTION OF THE METHOD

Figure 1:
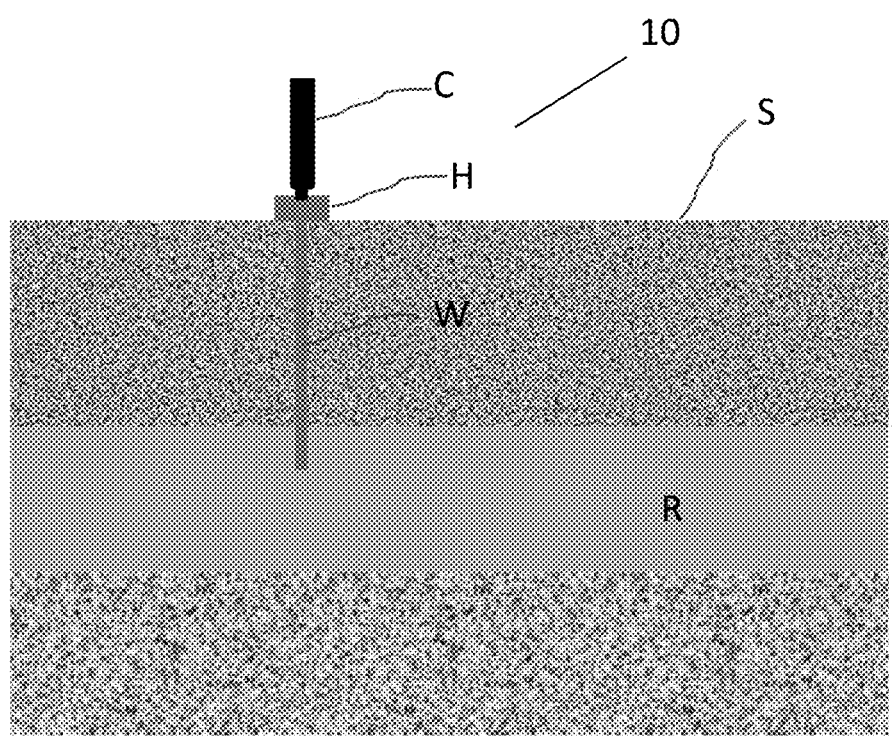
FIG. 1 illustrates a first embodiment of a method in accordance with the invention involving collection of water from a well in accordance with the invention.

In general, one of the applications of the invention relates to a method for the exploitation and/or monitoring of an underground formation having at least one reservoir comprising water, at least one gas species of interest and at least one atmospheric rare gas that are present in dissolved form in the water of the reservoir.

The present invention in particular determines the concentration of the gas species of interest in the water of the reservoir. The gas of interest to be exploited or monitored may be of the gaseous hydrocarbon type (such as methane), $CO_2$, hydrogen, sulfuric acid, etc.

The method according to the invention is based on the hypothesis that the underground water reservoir has been fed naturally with water in equilibrium of solubility with the air, in ambient conditions of pressure and temperatures. This signifies in particular that the water reservoir studied is initially (i.e. before any degassing) in equilibrium of solubility with the air, or in other words the initial content of dissolved gas in the reservoir (i.e. the content of dissolved gas in the water reservoir before natural or artificial degassing) corresponds to the equilibrium of solubility in water at ambient pressure and temperature of the atmospheric compounds. It should be noted that this hypothesis satisfies the most general case of aquifers.

Moreover, the method according to the invention is based on the hypothesis that the vapor phase resulting from the degassing of the water present in the underground water reservoir was produced at the equilibrium of solubility with the underground water reservoir.

Furthermore, the method according to the invention is based on a reference composition corresponding to the content of at least one atmospheric isotope of a rare gas, compared to the equilibrium of the water with the air in ambient conditions of pressure and temperatures. An atmospheric isotope of a rare gas is an isotope of a rare gas whose presence in the underground water reservoir can only have resulted from an equilibrium with the atmosphere. We may mention for example the following atmospheric isotopes: the $^{20}$Ne isotope for neon, the $^{36}$Ar isotope for argon and the $^{84}$Kr isotope for krypton.

These hypotheses allow determination of the concentration of the gas species of interest in the water of the reservoir, representative of the physical phenomena (while preserving the underlying physical reality), while still being simple to use.

On the basis of these hypotheses, it may then be considered that any compound in excess relative to a reference composition that would be of atmospheric origin corresponds to the addition of a constituent to the water reservoir. In fact, as the water reservoir is in equilibrium of solubility with the air, the atmospheric isotopes of the rare gases present in the water can only have resulted from the equilibrium of the water with the air. Consequently, the initial content of atmospheric isotope corresponds to the equilibrium of solubility of the atmospheric compounds in the water at ambient pressure and temperature. Thus, Henry's law, which is well known in the art, can validly be applied for determining the concentration of atmospheric gases in water. In fact, Henry's law defines the equilibrium of solubility according to the Henry constant $K_i$ for a compound i, as a function of the concentration of the compound in the vapor phase ($C^j_v$) and liquid phase ($C^j_l$), as follows:

$$C^j_v = C^j_l K_i \quad (1)$$

With the air is an infinite reservoir of fixed composition, the parameter $C^j_v$ is known for all of the atmospheric compounds. Moreover, the Henry coefficients for the compounds in the air as a function of the equilibrium temperature are well known (reference may be made for example to the document Gevantman, 2003). Thus, it is possible to determine the concentration of atmospheric gases in water $C^j_l$ by applying Henry's law.

Moreover, as the rare gases are intrinsically inert both chemically and biologically, their concentration in water can only vary as a result of physical processes such as diffusion, mixing and phase equilibria. Thus, the concentration of $^{20}$Ne, $^{36}$Ar and $^{84}$Kr isotopes in an underground water reservoir can only vary if the underground water reservoir becomes comparable to an open system in free exchange with a reservoir of fluid that is not equilibrated with the air in ambient conditions (which takes place for example when the water is brought into contact with water that is not equilibrated with the air, when the water has interacted with a fluid that is not equilibrated with the air, or when the water has undergone a phase change, notably formation of a vapor phase). If a water reservoir has never been subjected to one of the three conditions listed above, its concentration of atmospheric gases is predictable from Henry's law.

It is quite clear to a person skilled in the art that the above hypotheses are not limiting, and that it is possible to apply the method according to the invention to a water reservoir that would not fully satisfy at least one of the hypotheses expounded above. It is, however, quite clear that application of the method according to the invention to a water reservoir that would best satisfy the hypotheses expounded above would lead to a more reliable estimate of the concentration of the gas species of interest in the water of the reservoir.

The method according to the invention comprises at least the following steps:
1. Taking a gas sample at the surface
2. Analysis of the gas sample taken
3. Quantification of the dissolved gas The main steps of the present invention are detailed below.

1. Taking a Gas Sample at the Surface

In this step it is a matter of taking at least one gas sample at the level of at least one collection zone of the water of the underground reservoir, the zone being located at the surface of the underground formation. The collection of the water of the underground reservoir may be a passive collection when the water rises naturally from the reservoir to the surface by the effect of a pressure gradient, or it may require a well, optionally equipped with a pumping system when the natural pressure in the water reservoir is insufficient to cause the water to rise from the reservoir to the surface spontaneously.

Gas sampling may be carried out in various ways, depending on the type of water reservoir and how it is collected. The main constraint to be observed is to protect the sample against any contamination by the ambient air. For this purpose, the sample container must be properly water-tight and gas-tight, and must allow reliable storage between the time of sampling and the analysis in the laboratory. The term sampling cylinder is used hereinafter to denote the sample container.

According to one embodiment of the invention, a sampling cylinder is used having a tubular body made of metal or glass which is isolated from the exterior by a valve at each end.

According to one application of the method according to the invention to an aquifer equipped with a well and a pump, or to an artesian aquifer equipped with a well, or to a natural resurgence captured by a pipe or a well, the sampling cylinder which collects the gas sample is positioned at the well head. Thus, sampling is carried out at the surface, and not at the bottom of the well. Advantageously, sampling is carried out after scavenging of the sampling cylinder by the water stream generated by the pump (in the case of a well equipped with a pump) or the natural flow (in the case of an artesian well).

According to one application of the method according to the invention to a natural resurgence of water not equipped with a well, the sampling cylinder isolates the gas stream derived from the water from the ambient air. According to one embodiment of the invention, the sampling cylinder comprises a tubular body connected to a funnel at one of its ends, and the funnel may be made of glass, metal or plastic.

For this embodiment, capture of the resurgence is performed by presenting the portion of the sampling cylinder formed by the funnel at the level of the resurgence. In this way the gas brought out of solution in the water sweeps over the top of the funnel and the sampling cylinder and may thus be collected while avoiding any contamination with the ambient air.

2. Analysis of the Gas Sample Taken

In this step it is a matter of analyzing the gases sampled in the preceding step. According to the invention, at least the concentration of the gas species in question (for example a gaseous hydrocarbon (such as methane), $CO_2$, hydrogen, sulfuric acid) in the gas sample taken in the preceding step, as well as the concentration of at least one atmospheric isotope of at least one rare gas in the gas sample taken in the preceding step, are measured.

According to one embodiment of the invention, the species of interest in the gas sample is quantified by gas chromatography, by mass spectrometry, by infrared analysis, electrochemical analysis or by Raman interferometry. Knowledge of the manner of applying such techniques in order to measure the concentration of a gas species of interest is known. Reference may be made to (Gonzalez Penagos et al., 2016) and (Magnier et al., 2012) for more details about suitable methods of analysis for carrying out the invention.

According to one embodiment of the invention, the concentration of an atmospheric isotope of a rare gas in the gas sample taken in the preceding step is determined by mass spectrometry, notably in order to define the isotopic fraction that is properly atmospheric of the species in question. According to one embodiment of the invention, the atmospheric isotope considered is the $^{36}Ar$ isotope of argon, or the $^{20}Ne$ isotope of neon, or the $^{84}Kr$ isotope of krypton. According to one embodiment of the invention, the concentration of each of the following atmospheric isotopes is determined: $^{36}Ar$ isotope of argon, $^{20}Ne$ isotope of neon and $^{84}Kr$ isotope of krypton.

According to an embodiment of the invention in which one of the rare gases considered is argon, the concentration of atmospheric isotope of argon is determined by analysis by gas chromatography coupled to a mass spectrometer.

Advantageously, in addition to argon, the concentration of at least one atmospheric isotope of another rare gas, such as neon, argon, krypton, or xenon, is measured.

3. Quantification of the Dissolved Gas

In this step, the concentration of the gas species of interest present in dissolved form in the water of the reservoir in question is determined by a model that is a function of the concentration of at least the gas species being considered and of the concentration of at least one atmospheric isotope of a rare gas present in the gas sample taken in step 1 described above, with the aforementioned concentrations having been measured in step 2 described above.

According to a first embodiment of the invention, a model is used based on an analytical method for determining the concentration of the gas species of interest present in dissolved form in the water of the reservoir in question, from the concentrations of at least the gas species in question and of at least one atmospheric isotope present in the gas sample that was taken.

Alternatively, a model is used based on a numerical method for determining the concentration of the gas species of interest present in dissolved form in the water of the reservoir in question, from the concentrations of at least the gas species in question and of at least one atmospheric isotope present in the gas sample taken. These two embodiments are presented below.

The following notation is used hereinafter:
superscript i to denote a constituent relating to an atmospheric isotope;
superscript j to denote a constituent relating to the gas species of interest;
subscript l to denote a constituent in its liquid form;
subscript v to denote a constituent in its vapor form.

3.1. Analytical Method

According to the invention, implementation of the method according to the invention by a model based on an analytical method is based on the hypothesis according to which the water reservoir is in equilibrium of solubility with the air, or else that the vapor phase of any compound is generated at equilibrium, artificially or naturally, starting from a liquid phase.

According to one embodiment of the invention, an analytical approach is defined by assuming, in addition to the hypothesis, that:
the two-phase system (liquid and vapor) satisfies the general principles of conservation of mass and phase equilibria;
the total amount of species i is initially (before degassing) in dissolved form, and the volume of liquid is constant (only the volume of gas changes depending on the degree of supersaturation of the system).

Based on these hypotheses, the concentration $C^j_T$ of gas of interest dissolved in the water can be defined by a formula:

$$C^j_T = (1/K_{Hj} + C^i_{air}/(C^i_v \cdot K_{Hi}^{amb}) - 1/K_{Hi}^z) \cdot C^j_v \qquad (1)$$

where:
$K_{Hj}$ is the Henry constant relating to the known species of interest j;
$C^i_{air}$ is the concentration of the atmospheric isotope i in the air being measured;
$C^i_v$ is the concentration of the vapor phase of the atmospheric isotope i being measured;
$K_{Hi}^{amb}$ is the Henry constant at the ambient surface conditions (by default, 1 bar and 20° C.), which is known;
$K_{Hi}^z$ is the Henry coefficient of the constituent i at depth z, known; and
$C^j_v$ is the concentration of the gas species of interest in the vapor form being measured.

According to an embodiment of the invention in which the water reservoir is located at relatively small depths, it can be assumed that $K_{Hi}^z$ is close to $K_{Hi}^{amb}$, and equation (1) is simplified as follows:

$$C^j_T = (1/K_{Hj} + (C^i_{air}/C^i_v - 1)/K_{Hi}^{amb}) \cdot C^j_v \qquad (2)$$

Thus, the analytical method and its variants of execution as described above make it possible to determine the concentration of species j in the initial system (i.e. before degassing, whether artificial or natural) based only on the content of compound i and j in the vapor phase measured at the surface, knowing a priori the Henry coefficients for these two constituents, and the concentration of compound i in the air.

3.2. Numerical Method

According to the invention, the third step of the method according to the invention can be carried out by a model based on a numerical method based on the hypothesis according to which the water reservoir is in equilibrium of solubility with the air, or else that the vapor phase of any compound is generated at equilibrium, artificially or naturally, starting from a liquid phase.

The numerical method according to one embodiment of the invention makes it possible to determine the concentration of the gas species of interest present in dissolved form in the water of the reservoir in question, starting from the concentration of at least the gas species in question and the concentration of at least one atmospheric isotope present in the gas sample taken.

In general, the numerical method that can be used for solving step 3 of the method according to the invention is based on an iterative inverse method, comprising solution of a direct problem at each iteration and optimization of an objective function (which may correspond to minimization or finding zero of the objective function) by measuring a difference between measured values and values calculated by solving the direct problem.

Solution of the Direct Problem

According to one embodiment of step 3 of the present invention, the direct problem of the numerical method is based on equations of state. According to a variant embodiment of step 3 of the present invention, a numerical method is used based on the equations of state as defined in the documents (Soreide and Whitson, 1992) and (Kontogeorgis et al., 1996). These equations make it possible to describe the composition, the density and the state of the phases of systems comprising at least water ($H_2O$), compound i and compound j.

According to one embodiment of the invention, a numerical method is used based on the equations of state as described in (Soreide and Whitson, 1992), but extended to the rare gases. In particular, step 3 of the present invention is carried out on the basis of a formula of the type:

$$P = \frac{RT}{v-b} - \frac{aT}{v^2 + 2bv - b^2} \quad (3)$$

where:
P is the pressure of the system;
T is the temperature of the system;
v is the molar volume;
b is the covolume of the system, which depends on the individual covolume of each compound; and
a is a constant of the equation of state.

According to one embodiment of the invention, the constant a as defined above describes the interactions between the compounds, and is proportional to the mole fraction of each compound, to their thermodynamic properties, and to parameters of binary interactions. According to one embodiment of the invention, constants aVAP and aAQ are defined respectively for the vapor and liquid phases of the compound in question according to formulas:

$$a^{VAP} = \sum_i \sum_j y_i y_j \sqrt{a_i a_j} \, 1 - k_{ij}^{VAP} = \sum_i \sum_j y_i y_j a_{ij}^{VAP}.$$
$$a^{AQ} = \sum_i \sum_j x_i x_j \sqrt{a_i a_j} \, 1 - k_{ij}^{AQ} = \sum_i \sum_j x_i x_j a_{ij}^{AQ}. \quad (4)$$

with $$a_i = 0.45724 \frac{R^2 T_{C,i}^2}{P_{C,i}} \alpha T_{r,i}$$

$T_{C,i}$ is the critical temperature for compound i;
$T_{r,i}$ is the critical temperature for compound i;
$\alpha$ is a parameter of the equation of state;
$k_{ij}$ are the parameters of binary interactions, for the vapor phase (superscript VAP) and for the liquid phase (superscript AQ); and
$x_i$, $x_j$ and $y_i$, $y_j$ are the mole fractions of the compounds i and j in the vapor and liquid phases.

Definition of the Objective Function

According to one embodiment of the invention, it is necessary to determine the concentration of the gas species of interest $C^j_T$ as a function of the ratio of the concentration $C^i_v$ of atmospheric isotope of rare gas i measured in the sample taken in step 1 to the concentration $C^j_v$ of the species of interest j measured in step 2 in the sample taken in step 1. According to this embodiment, an objective function can be defined in the form of an equation:

$$f(C^j_T) = [C^i_v/C^j_v]_m - g(P,T,s,C^j_T) \quad (5)$$

where T is the temperature, P is the pressure, s is the salinity and $g(P, T, s, C^j_T)$ is a function corresponding to a model of equation of state whose result, for a given value of concentration $C^j_T$ of gas of interest dissolved in the water, corresponds to the calculated value $[C^i_v/C^j_v]_c$. At each iteration, this value $[C^i_v/C^j_v]_c$ is compared with the measured value $[C^i_v/C^j_v]_m$ that corresponds to the ratio of the concentration $C^i_v$ of atmospheric isotope of rare gas i measured in the sample taken in step 1 to the concentration $C^j_v$ of the species of interest j measured in step 2 in the sample taken in step 1.

Optimization of the Objective Function

According to one embodiment of the invention, optimization of the objective function is solved by the dichotomy method. The dichotomy method makes it possible, by an application of an iterative mathematical algorithm, to identify the value x such that $f(x)=0$, where f is a continuous real function over an interval [Vmin, Vmax] and Vmin and Vmax are two real numbers. For this purpose, at a given iteration, the dichotomy method splits the interval of the current iteration and keeps, for the next iteration, that one of the two sub-intervals in which there is a zero of the function. Advantageously, the real numbers Vmin and Vmax are initialized so that $f(Vmin)$ and $f(Vmax)$ are of opposite sign.

According to an embodiment of the invention based on an objective function $f$ defined in the form of equation (4) described above, identification of $f(C^j_T)=0$ corresponds to identification of the set of parameters ($P, T, s, C^j_T$) satisfying the value measured in the sample. The variables P, T and s being fixed and given by the user, only variable $C^j_T$ has to be found by the dichotomy method. For this purpose, a domain of variation [Vmin, Vmax] is defined relative to variable $C^j_T$, and the value of the variable $C^j_T$, within this interval, that makes it possible to minimize the objective function, is found by the dichotomy method. Advantageously, this iterative process is stopped when a predefined stop criterion is reached. This criterion may correspond to a maximum acceptable value of the objective function (for example the iterative process is stopped when the estimate of the objective function is below a threshold predefined by the expert), or else to a maximum number of iterations of the iterative process. According to an alternative embodiment of the invention, a stop criterion is defined based on a maximum acceptable value of the relative difference of the function $f$ between the values [Vmin, Vmax] of the current iteration. A threshold may be defined which is designated ε and stopping the iterative process when, at a given iteration, ($f(Vmin)$–

$f(V_{max}))/f(V_{min})<\varepsilon$. For example, $\varepsilon=0.05$ may be defined for a tolerance on convergence of the algorithm of 5%. Thus, once the criterion of convergence is reached, the solution obtained by the numerical method properly reproduces the total composition of species i of the initial system, as well as the compositions, densities and molar volumes of the vapor and liquid phases of the species j at given pressure, temperature and salinity.

Thus, at the end of this step, whether it has been solved by an analytical method, by a numerical method or by any other method, the concentration is obtained of the gas species of interest present in dissolved form in the water of the reservoir in question, starting from the concentration of at least the gas species in question and the concentration of at least one atmospheric isotope present in the gas sample taken in step 1, the aforementioned concentrations having been measured in step 2.

The concentration of a gas of interest in a water reservoir is valuable information for deciding on exploitation of the species in question, or, in the case of reservoir monitoring, for understanding contamination of the reservoir by industrial activity (pollution of an aquifer for example) or by a natural process (seismicity, hot springs, etc.). Moreover, the gas burden of water reservoirs may be essential information for production of a thermal energy reservoir (geothermal energy).

Determination of the Phase State

This is an optional step that determines the phase state of the gas species in question in the water reservoir in question, starting from the concentration of the gas species j and its saturation in the water. In other words, it is a matter of determining whether the species of interest j is present in the single-phase or two-phase form in the water reservoir in question.

According to an embodiment of the invention in which the gas of interest is methane, the model described in the documents (Duan et al., 1992; Duan et al., 2006) can be used to define the saturation of gas of interest j in the water.

According to an embodiment of the invention according to which it is considered that the ideal gas law is applicable and that the pressure P varies with the depth z according to a law: $P=P_0+\square\square g\cdot z$, where $P_0$ is atmospheric pressure, $\square$ is the density of water ($\square\square\square\square\square\square\square x\square\square^{\square}\square kg/m^3$), g is gravitational attraction ($g=9.81$ m²/s) and z is the depth of water (in meters) from the surface to the underground water reservoir in question, the saturation $S_j$ of gas of interest j in the water of the underground water reservoir can be determined from a formula:

$$S_j=[(1/K_{Hj}+(C^i_{air}/C^j_v-1)/K^{amb}_{Hi})\cdot C^j_v-C^j_{sat}]\cdot R(T_0+z\cdot G_T)/(\square\square g\cdot z+P_0) \quad (6)$$

where:
- $K_{Hj}$ is the Henry constant relating to the species of interest j, which is known;
- $C^i_{air}$ is the concentration of the atmospheric isotope i in the air, which is known or measured;
- $C^j_v$ is the concentration of the vapor phase of the atmospheric isotope i measured in the sample taken;
- $K_{Hi}^{amb}$ is the Henry constant in the ambient surface conditions (by default, 1 bar and 20° C.), which is known;
- $K_{Hi}^z$ is the Henry coefficient of constituent i at depth z, which is known;
- $C^j_v$ is the concentration of the gas species of interest j in the vapor form;
- $C^j_v$ is the concentration of the gas species of interest j at saturation for a given pair (P,T).

Starting from the saturation $S_j$ of gas of interest j in the water of the underground water reservoir, it is possible to deduce the phase state of the system by assuming that the supersaturation of species j corresponds to an excess concentration $C^j_{exc}$ of this species, defined as $C^j_{exc}=C^j_T-C^j_{sat}$. After determining the concentration of the gas species of interest in the water of the reservoir, a step of exploitation of the underground formation may be implemented as a function of the concentration determined, for example, drilling a new well, injecting a fluid via an injection well, etc. Alternatively, in the context of monitoring an underground formation, for example a $CO_2$ storage site, a corrective or preventive step can be performed to prevent any contamination. For example, this step may be a remediation of a well.

EXAMPLE OF APPLICATION

FIG. 1 illustrates a first embodiment 10 of the invention in which collection of water is performed from a water reservoir R from a well W which connects the surface S of the formation with the water reservoir R. The sampling of the water is performed with a sampling cylinder placed at the head of the well H of the well.

Figure 2:
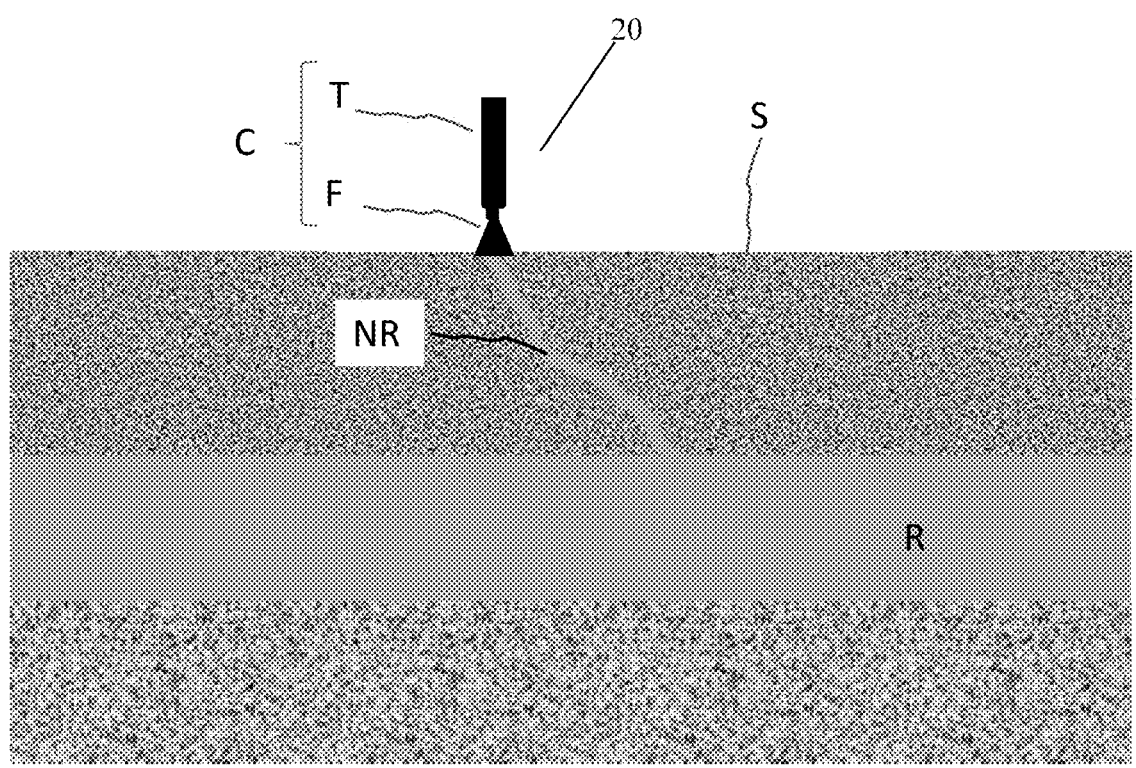
FIG. 2 illustrates a second embodiment of a method in accordance with the invention.

FIG. 2 illustrates a second embodiment 20 of the invention in which collection of water is carried out at a level NR of natural resurgence of the water reservoir R of the formation in which sampling is carried by using a sampling cylinder including at least one tubular body T connected to a funnel F.

The features and advantages of the method according to the invention will become clearer on reading the example of application given below.

A water reservoir of an underground formation corresponding to a methane-rich aquifer located at a depth of 400 meters and equipped with a well is considered for this example. As the water rises from the aquifer to the surface via the drilled well, the water is degassed and generates a vapor phase. A sample of gas is taken at the well head by a stainless-steel sampling cylinder isolated by high-pressure valves. Sampling is carried out in ambient conditions (10° C., 1 bar). For carrying out the method according to the invention, the atmospheric isotope $^{36}$Ar of argon is used, and the gas of interest whose concentration in the aquifer is to be determined is methane.

This sample is analyzed by gas chromatography to determine the methane composition of the gas sampled, as well as by mass spectrometry to determine its concentration of $^{36}$Ar. The concentrations obtained for methane and for the atmospheric isotope $^{36}$Ar of argon are $y_{CH4}=92.8$ vol % and $y^{36}Ar=3.5\times10^{-4}$ vol % respectively.

According to a first embodiment of the method according to the invention, a model is used based on a numerical method. More precisely, in order to acquire information corresponding to the compositional state of the system in the aquifer, a variant of the numerical method is used based on an extension of the model of Soreide & Whitson (1992) as described in substep 3.2. For this purpose, the hydrostatic pressure of the aquifer is defined (and therefore its depth and its artesian loading if applicable) and the content of isotope $^{36}$Ar determined above is taken as a reference composition compared to the equilibrium of water with air at 1 bar and at a mean annual surface temperature (10° C.), without excess of air, and without oxygen.

The variant of the numerical method used allows faithful calculation of the fractionation of this reference constituent between the liquid phase and the vapor phase for all equilibria, and the concentration of atmospheric $^{36}$Ar in the vapor phase (therefore the phase that is analyzed in this study) makes it possible to determine the abundance of the component at equilibrium in the aquifer, relative to a so-called excess component. The excess component to be quantified here is methane.

Application of the variant embodiment of the numerical method as described above makes it possible to obtain a total number of moles of methane present in the aquifer of 11.9 mol·m$^{-3}$.

For comparison, application of a variant of the analytical method as defined by equation (2) described in substep 3.1 leads to a total number of moles of methane present in the aquifer of 12.1 mol·m$^{-3}$.

Thus, it can be seen that the two methods numerically and analytically, predict very similar concentrations of gas dissolved in the water reservoir being studied.

Thus, the method according to the invention makes determination of the concentration of a gas of interest present in an underground water reservoir starting from sampling carried out at the surface of the formation, and analysis of this sample, comprising measurement of the concentration of this gas of interest in the sample and the concentration of at least one atmospheric isotope of at least one rare gas in this sample.

In general, this method is particularly advantageous for monitoring underground water tables, notably making complex sampling unnecessary, or the well production tests usually carried out in this context. In fact, this method allows easier monitoring of natural or industrial contamination by various gaseous species from these waters located near sites of exploration or exploitation of resources, such as activities of gas storage, gas production, geothermal energy activities, or other activities.

The invention claimed is:

1. A method for exploitation and/or monitoring an underground formation having at least one reservoir comprising water, at least one gas species and at least one atmospheric isotope of at least one rare gas that is present in dissolved form in the water of the reservoir, comprising:
   i) sampling at least one gas sample at a level of a collecting zone of the water of the reservoir located at a surface of the formation, the sampling being carried out while avoiding contamination with air;
   ii) measuring at least a concentration of at least one gas species and a concentration of at least one atmospheric isotope of rare gas in the gas sample;
   iii) determining the concentration of at least one of the gas species dissolved in the reservoir by a model, the model being a function of at least one concentration of at least one gas species in at least one gas sample and of the concentration of at least one atmospheric isotope in the gas sample; and
   iv) exploiting the underground formation, in response to the determined concentration of at least one gas species dissolved in the reservoir determined by the model, by drilling a new well and/or injecting a fluid via an injection well and/or monitoring the underground formation and performing a corrective or preventive step according to the determined concentration of the at least one gas species dissolved in the reservoir determined by the model to prevent contamination of the formation; and
   wherein the model is based on an analytical method based on a formula:

$$C^j_T = (1/K_{Hj} + C^i_{air}/(C^i_v \cdot K_{Hi}^{amb}) - 1/K_{Hi}^z) \cdot C^j_v$$

where:
$C^j_T$ is the concentration of the gas species of interest j;
$K_{Hj}$ is the Henry constant relating to at least one gas species of interest j;
$C^i_{air}$ is a concentration of the atmospheric isotope i in air;
$C^i_v$ is the concentration of the atmospheric isotope i measured in at least one sample;
$K_{Hi}^{amb}$ is the Henry constant relating to the atmospheric isotope i for ambient surface conditions;
$K_{Hi}^z$ is the Henry coefficient of the atmospheric isotope i at depth z; and
$C^j_v$ is the concentration of at least one gas species of interest j measured in the sample.

2. The method as claimed in claim 1, wherein at least one atmospheric isotope of the rare gas is at least one of $^{20}$Ne isotope of neon, $^{36}$Ar isotope of argon or $^{84}$Kr isotope of krypton.

3. The method as claimed in claim 2, wherein the collection of the water from the reservoir is from a well connecting the surface of the formation and the water reservoir, and wherein the sampling is carried out using a sampling cylinder placed at a head of the well.

4. The method as claimed in claim 3, wherein the collection of the water is by passive collection, carried out at a level of a natural resurgence of the water of the reservoir at the surface without a well, and in which the sampling is carried out by using a sampling cylinder comprising at least one tubular body connected to a funnel, the gas sample being taken at a level of the funnel.

5. The method as claimed in claim 2, wherein the collection of the water is by passive collection, carried out at a level of a natural resurgence of the water of the reservoir at the surface without a well, and in which the sampling is carried out by using a sampling cylinder comprising at least one tubular body connected to a funnel, the gas sample being taken at a level of the funnel.

6. The method as claimed in claim 2, wherein the model is based on an iterative numerical method comprising solving a direct problem at each iteration of the iterative numerical method and optimizing an objective function measuring a difference between measured concentrations and concentrations calculated by solving of the direct problem.

7. The method as claimed in claim 1, wherein the collection of the water from the reservoir is from a well connecting the surface of the formation and the water reservoir, and wherein the sampling is carried out using a sampling cylinder placed at a head of the well.

8. The method as claimed in claim 7, wherein the collection of the water is by passive collection, carried out at a level of a natural resurgence of the water of the reservoir at the surface without a well, and in which the sampling is carried out by using a sampling cylinder comprising at least one tubular body connected to a funnel, the gas sample being taken at a level of the funnel.

9. The method as claimed in claim 7, wherein the model is based on an iterative numerical method comprising solving a direct problem at each iteration of the iterative numerical method and optimizing an objective function measuring a difference between measured concentrations and concentrations calculated by solving of the direct problem.

10. The method as claimed in claim 1, wherein the collection of the water is by passive collection, carried out at a level of a natural resurgence of the water of the reservoir at the surface without a well, and in which the sampling is carried out by using a sampling cylinder comprising at least one tubular body connected to a funnel, the gas sample being taken at a level of the funnel.

11. The method as claimed in claim 10, wherein the model is based on an iterative numerical method comprising solving a direct problem at each iteration of the iterative numerical method and optimizing an objective function measuring a difference between measured concentrations and concentrations calculated by solving of the direct problem.

12. The method as claimed in claim 1, wherein the model is based on an iterative numerical method comprising solving a direct problem at each iteration of the iterative numerical method and optimizing an objective function measuring a difference between measured concentrations and concentrations calculated by solving of the direct problem.

13. The method as claimed in claim 12, wherein the direct problem is solved by use of at least one equation of state.

14. The method as claimed in claim 13, wherein the optimization of the objective function is carried out by a dichotomy method.

15. The method as claimed in claim 12, wherein the optimization of the objective function is carried out by a dichotomy method.

* * * * *